US008532931B2

(12) United States Patent
Lakatos

(10) Patent No.: US 8,532,931 B2
(45) Date of Patent: Sep. 10, 2013

(54) CALCULATING SAMPLE SIZE FOR CLINICAL TRIAL

(76) Inventor: Edward Lakatos, Croton-on-Hudson, NY (US)

( * ) Notice: Subject to any disclaimer, the term of this patent is extended or adjusted under 35 U.S.C. 154(b) by 747 days.

(21) Appl. No.: 12/205,889

(22) Filed: Sep. 7, 2008

(65) Prior Publication Data

US 2010/0063741 A1   Mar. 11, 2010

(51) Int. Cl.
*G06F 7/00* (2006.01)
(52) U.S. Cl.
USPC ................ 702/19; 702/20; 703/12; 703/13; 707/700

(58) Field of Classification Search
None
See application file for complete search history.

(56) References Cited

U.S. PATENT DOCUMENTS

| | | | |
|---|---|---|---|
| 6,041,788 A * | 3/2000 | Shen | 128/898 |
| 6,218,129 B1 | 4/2001 | Walsh et al. | |
| 7,269,516 B2 | 9/2007 | Brunner et al. | |
| 2002/0023083 A1 | 2/2002 | Durkalski | |
| 2002/0165762 A1 | 11/2002 | Goldman et al. | |
| 2003/0046110 A1 | 3/2003 | Gogolak | |
| 2003/0065669 A1 | 4/2003 | Kahn et al. | |
| 2003/0108938 A1 | 6/2003 | Pickar et al. | |
| 2005/0251011 A1 | 11/2005 | Zahlmann et al. | |
| 2005/0256745 A1 | 11/2005 | Dalton | |
| 2006/0143047 A1 | 6/2006 | Briegs et al. | |
| 2006/0248031 A1 | 11/2006 | Kates et al. | |
| 2007/0027636 A1 | 2/2007 | Rabinowitz | |
| 2008/0038833 A1 | 2/2008 | Popp | |
| 2008/0040151 A1 | 2/2008 | Moore | |
| 2008/0065418 A1 | 3/2008 | Byrom et al. | |

OTHER PUBLICATIONS

Wittes, J; "Sample Size Calculations for Randomized Controlled Trials"; Epidemiologic Reviews; vol. 24; No. 1; pp. 39-53; 2002.
Lakatos, E; "Sample Size Determination in Clinical Trials with Time-Dependent Rates of Losses and Noncompliance"; Controlled Clinical Trials; vol. 7; pp. 189-199; 1986.
Lakatos, E; "Sample Size Based on the Log-Rank Statistic in Complex Clinical Trials"; Biometrics; No. 44; pp. 229-241; Mar. 1988.
Lakatos, E; "A Comparison of Sample Size Methods for the Logrank Statistic"; Statistics in Medecine; vol. 11; pp. 179-191; 1992.
Lakatos, E; "Designing Complex Group Sequential Survival Trials"; Statistics in Medecine; vol. 21; pp. 1969-1989; 2002.
Barthel, F; Babiker, A; Royston, P; Parmar, M; "Evaluation of Sample Size and Power for Multi-Arm Survival Trials Allowing for Non-Uniform Accrual, Non-Proportional Hazards, Loss to Follow-Up and Cross-Over"; Statistics in Medecine; vol. 25; pp. 2521-2542; 2006.
Bouezmarni, T; Rombouts, V; "Density and Hazard Rate Estimation for Censored and α-Mixing Data using Gamma Kernels"; HEC Montreal; Nov. 19, 2006.
Borenstein, M; Rothstein, H; Cohen, J; Schoenfeld, D; Berlin, J; Lakatos, E; "Power and Precision: a Computer Program for Statistical Power Analysis and Confidence Intervals"; Taylor and Francis; Chap. 21; pp. 181-205.
Hintze, J; "PASS 2005 User's Guide III"; Kaysville, UT; NCSS; pp. 700-001 to 700-008 and pp. 705-001 to 705-014; 2005.
Lachin, J; Foulkes, M; Evaluation of Sample Size and Power for Analyses of Survival with Allowance for Nonuniform Patient Entry, Losses to Follow-Up, Noncompliance, and Stratification; Biometrics; vol. 42; pp. 507-519; Sep. 1986.
Wu, M; Fisher, M; Demets, D; "Sample Sizes for Long-Term Medical Trial with Time-Dependent Dropout and Event Rates"; Controlled Clinical Trials; vol. 1; pp. 109-121; 1980.
Halpern, J; Brown Jr, B; "A Computer Program for Designing Clinical Trials with Arbitrary Survival Curves and Group Sequential Testing"; Controlled Clinical Trials; vol. 14; pp. 109-122; 1993.
Shih, J; "Sample Size Calculation for Complex Clinical Trials with Survival Endpoints"; Controlled Clinical Trials; vol. 16; pp. 395-407; 1995.
Gu, M; Lai, T; "Determination of Power and Sample Size in the Design of Clinical Trials with Failure-Time Endpoints and Interim Analyses"; Controlled Clinical Trials; vol. 20; pp. 423-438; 1999.
SAS Institute Inc.; 2004; SAS/STAT; 9.1 User's Guide; Cary; NC: SAS Institute Inc.; p. 3563.

* cited by examiner

*Primary Examiner* — Mary Zeman
(74) *Attorney, Agent, or Firm* — Mark Terry

(57) ABSTRACT

A method for calculating a sample size for a clinical trial of a first treatment can be provided. The method can include reading a survival curve from a clinical trial for a second treatment, wherein the clinical trial may be selected by a user interacting with a user interface. The method can further include selecting a plurality of points on the survival curve and storing coordinates for each of the plurality of points, wherein the plurality of points are selected so as to capture substantial features of the survival curve. Then, a hazard curve is generated based on the coordinates that were stored, wherein the hazard curve may be a step function. The method can further include calculating a sample size for the clinical trial of the first treatment using a Markov model based on the hazard curve.

14 Claims, 5 Drawing Sheets

CALCULATING SAMPLE SIZE FOR CLINICAL TRIAL

STATEMENT REGARDING FEDERALLY SPONSORED RESEARCH OR DEVELOPMENT

This invention was made with Government support under a contract awarded by the National Institute of Health. The Government has certain rights in this invention.

BACKGROUND OF THE INVENTION

1. Field of the Invention

The present invention relates to the field of medical informatics, and more particularly to a method for using already existing clinical trial data to calculate figures for use in a new clinical trial.

2. Description of the Related Art

In the pharmaceutical industry, time to market is often the most important factor driving pharmaceutical profitability. In the U.S. alone, a huge percentage of total annual pharmaceutical research and development funds are spent on human clinical trials. Further, spending on clinical trials is growing with each passing year as trials increase both in number and complexity. A clinical trial refers to an investigation of safety and efficacy of a treatment for a disease or affliction, which treatment may include the use of drugs, counseling and/or other forms of therapy.

An analysis of the new treatment development process shows a major change in the drivers of time and cost. The discovery process, which formerly dominated time to market, has undergone a revolution due to techniques such as combinatorial chemistry and high-throughput screening. The regulatory phase has been reduced due to Federal Drug Administration (FDA) reforms and European Union harmonization. In their place, human clinical trials have become the main bottleneck. The time required for clinical trials accounts for a substantial amount of the time required for the average new treatment to come to market.

The conduct of clinical trials has changed remarkably little since trials were first performed. Clinical research remains largely a manual, labor-intensive, paper based process reliant on a cottage industry of physicians in office practices and academic medical centers. A typical clinical trial begins with the construction of a clinical protocol, a document which describes how a trial is to be performed, what data elements are to be collected, and what medical conditions need to be reported immediately to the pharmaceutical sponsor and the FDA. The clinical protocol and its authors are the ultimate authority on every aspect of the conduct of the clinical trial. This document is the basis for every action performed by multiple players in diverse locations during the entire conduct of the trial. Any deviations from the protocol specifications, no matter how well intentioned, threaten the viability of the data and its usefulness for an FDA submission.

The appropriate sample size of a clinical trial is a major component of the clinical protocol. Many other aspects of the clinical trial, including how the trial will be organized, how many health care providers are needed, the number of treatment centers required, and the number of countries involved depend on the sample size of the clinical trial. Further, the selection of an appropriate sample size is crucial to the outcome of the clinical trial. A sample size that is too small may fail to detect small treatment effects, but a sample size that is too large increases costs exponentially, thereby jeopardizing the completion and/or execution of the clinical trial.

Trials that evaluate the effect of treatments on survival are considered particularly important, not only because the outcome is so important, but also because the sample sizes are usually very large, and the trials very long. A trial to assess the ability of a drug to reduce blood pressure requires at most a few hundred patients, each observed for 8-12 weeks, while assessing the same drug's ability to reduce mortality might require 10,000 or more patients for 4-6 years. Survival trials can be used to evaluate not only a treatment's ability to extend time to death, but time to heart attack, cancer, development of AIDS, etc. The term "event" refers to the broader category that includes other outcomes such as heart attack, cancer, etc. in addition to "death".

When statisticians design survival trials, they typically utilize survival curves from prior trials and record the readily available probability of surviving, say, at the end of those trials. They routinely ignore the wealth of information hidden in the entire survival curve, which is more difficult to extract.

Survival curves are a valuable way to summarize trial results, enabling clinicians to visualize cumulative effects at the end of the trial. However, those summaries do not reveal how the level of risk changed as the trial progressed. If patients enter a trial upon arriving in the emergency room after initial signs of a heart attack, initial risk might be quite high, diminishing as critical periods pass. If patients enter a different trial after their physicians discover increased blood pressure, the initial risk might be rather low, increasing as the patients age. Unlike the survival curve which shows only cumulative effects, the hazard curve shows how risk changes with time.

When trials of good treatments fail due simply to inadequate sample size, the costs for both society and the trial sponsor (usually a pharmaceutical company or the U.S. Federal Government) are extremely high. On the one hand, the treatment may erroneously appear ineffective, and development abandoned. Not only are all the time, effort and resources invested wasted, but patients who could benefit from the treatment may be denied life-saving therapy. Alternatively, the sponsor may still believe the treatment works. If the decision is that the trial should be re-run, this time with adequate sample size, the costs will be larger than the first time. But the biggest loss in this situation is the time necessary to get the new trial planned, initiated and completed. For a treatment with a billion dollar yearly revenue potential, such delays cost in excess of three million dollars each day. And these delays can last for years.

The presently available software tools in the pharmaceutical industry address various portions of the clinical protocol design process and the clinical trial process as a whole. In particular, software tools for calculating sample size are available. Some of these software tools allow users to enter time-dependent failure rates. Some allow a user to utilize a Markov model approach, while others allow a user to utilize simulation methods. None of the above software tools, however, address the issue of harnessing already existing clinical trial data to calculate an appropriate sample size for a new clinical trial.

Therefore, there is a need to overcome the deficiencies with the prior art and more particularly for a more effective way to calculate an appropriate sample size for a clinical trial using already existing clinical trial data.

BRIEF SUMMARY OF THE INVENTION

Embodiments of the present invention address deficiencies of the art in respect to medical informatics and provide a novel and non-obvious method and computer program product for calculating the appropriate sample size for a clinical trial of a treatment based on already-existing clinical trial data. In an embodiment of the invention, a method for calculating a sample size for a clinical trial of a first treatment can be provided. The method can include reading a survival curve from a clinical trial for a second treatment and selecting a plurality of points on the survival curve. The method can further include storing coordinates for each of the plurality of points and generating a hazard curve based on the coordinates that were stored. The method can further include calculating a sample size for the clinical trial of the first treatment using a Markov model based on the hazard curve.

In another embodiment of the invention, a computer program product comprising a computer usable medium embodying computer usable program code for calculating a sample size for a clinical trial of a first treatment is disclosed. The computer program product includes computer usable program code for reading a survival curve from a clinical trial for a second treatment and selecting a plurality of points on the survival curve. The computer program product further includes computer usable program code for storing coordinates for each of the plurality of points and generating a hazard curve based on the coordinates that were stored. The computer program product further includes computer usable program code for calculating a sample size for the clinical trial of the first treatment using a Markov model based on the hazard curve.

In another embodiment of the invention, an alternative method for calculating a sample size for a clinical trial of a first treatment can be provided. The method can include reading a survival curve from a clinical trial for a second treatment and selecting a plurality of points on the survival curve. The method can further include storing coordinates for each of the plurality of points, generating a hazard curve based on the coordinates that were stored and smoothing the hazard curve. The method can further include calculating a sample size for the clinical trial of the first treatment using a simulation method based on the hazard curve.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the present invention address deficiencies of the art in respect to medical informatics and provide a novel and non-obvious method and computer program product for calculating the appropriate sample size for a clinical trial of a treatment based on already-existing clinical trial data. In an embodiment of the invention, a method for calculating a sample size for a clinical trial of a first treatment can be provided. The method can include reading a survival curve from a clinical trial for a second treatment, where the second-treatment may or may not be identical to the first treatment. The method can further include selecting a plurality of points on the survival curve and storing coordinates for each of the plurality of points, wherein the plurality of points are selected so as to capture substantial features of the survival curve. Then, a hazard curve is generated based on the coordinates that were stored, wherein the hazard curve may be a step function. The method can further include calculating a sample size for the clinical trial of the first treatment using a Markov model based on the hazard curve.

Figure 1:
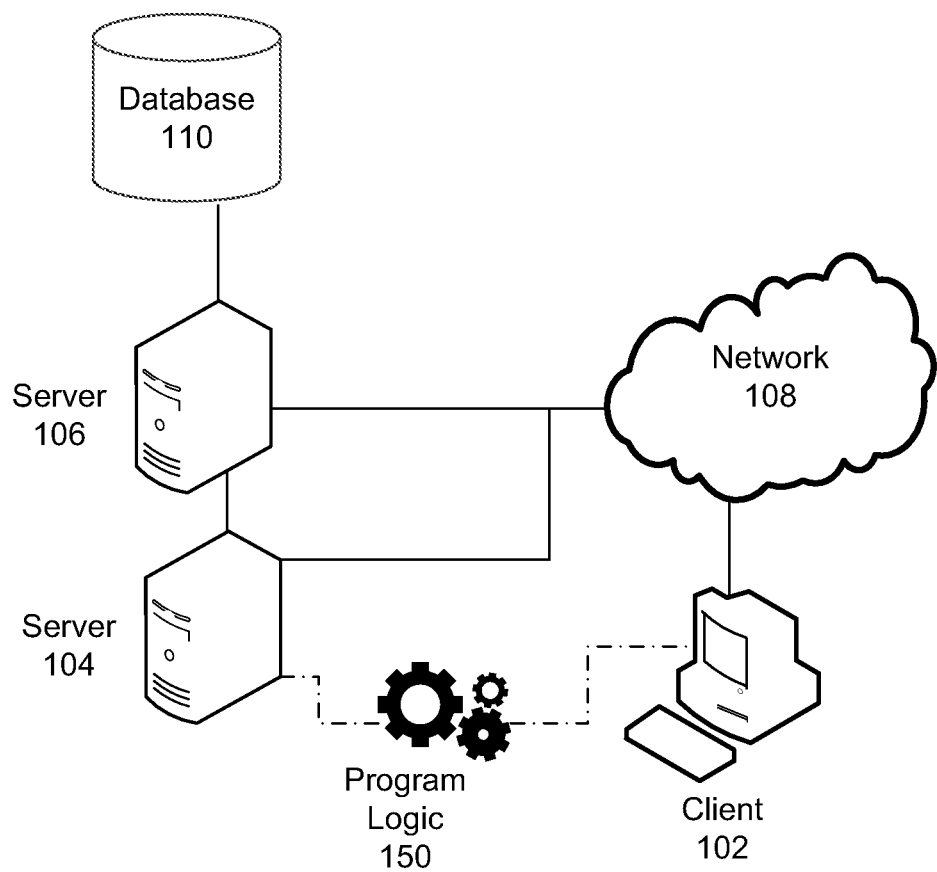
FIG. 1 is a block diagram illustrating a network architecture of a system for calculating the sample size of a clinical trial based on already existing clinical trial data, in accordance with one embodiment of the present invention.

Referring now to the drawing figures in which like reference designators refer to like elements, there is shown in FIG. 1 a block diagram illustrating a network architecture of a system for calculating the sample size of a clinical trial based on already existing clinical trial data, in accordance with one embodiment of the present invention. The exemplary embodiments of the present invention adhere to the system architecture of FIG. 1. FIG. 1 shows an embodiment of the present invention wherein a client user 102 may interact with servers 104-106 over a network 108, such as the Internet, the World Wide Web, a WAN or a LAN.

FIG. 1 shows client user 102 and servers 104-106 connected to network 108 via computers, such as desktop personal computers, workstations or servers. Servers 104, 106 may include software engines that deliver data and/or user interface component functionality to client computer 102. The servers 104-106 may adhere to any commercially available server platform, such as the Sun Microsystems J2EE platform, a Web-based application platform, an integrated platform for e-commerce or a content management system platform. It should be noted that although FIG. 1 shows only one client user 102 and two servers 104-106, the system of the present invention supports any number of client users and servers connected via network 108.

FIG. 1 shows a system whereby a client application, represented by program logic 150, running on a client 102 automatically displays a user interface for calculating the sample size of a clinical trial based on already existing clinical trial data. The user interface may or may not include information received from servers 104-106. Program logic 150 comprises computer source code, scripting language code or interpreted language code that is compiled to produce computer instructions that perform various functions of the present invention. In one embodiment of the present invention, the program logic 150 is a scripting language, such as ECMAScript, Cascading style sheets, XML, XSLT, Javascript, AJAX, XUL, JSP, PHP, and ASP, which runs in a web browser.

As explained above, program logic 150 may reside and execute solely on a client 102 and solely utilize data stored on client 102. Alternatively, the data may be requested and received from database 110 via database server 106. In this embodiment, the program logic 150 may be distributed to the client 102 via a CD, other removable media, download via network 108 or the like.

In another embodiment of the present invention, program logic 150 may reside and execute solely on server 104, wherein program logic 150 is provided to client 102 via an Application Service Provider (ASP) model. ASP is a business model that provides computer-based services to customers over a network. The application software resides on the vendor's system and is typically accessed by users through a web browser using HTML or by special purpose client software provided by the vendor. Custom client software can also interface to these systems through XML APIs. In this embodiment, the data used by program logic 150 may reside solely on the server 104 or the data may be requested and received from database 110 via database server 106 and also from client 102.

In another embodiment of the present invention, the program logic 150 may be distributed in a distributed computing scheme among server 104, client 102 and server 106, or any combination of the three. In yet another embodiment of the present invention, the program logic 150 is a client-server application having a client portion that resides on the computer of client user 102 and a server application that resides on a server, such as servers 104-106. Note that in one alternative, server 106 and 104 are logically connected or, further, integrated into one computing entity.

In an embodiment of the present invention, the computer systems of client user 102 and servers 104-106 are one or more Personal Computers (PCs), Personal Digital Assistants (PDAs), hand held computers, palm top computers, lap top computers, smart phones, game consoles or any other information processing devices. A PC can be one or more IBM or compatible PC workstations running a Microsoft Windows or LINUX operating system, one or more Macintosh computers running a Mac OS operating system, or an equivalent. In another embodiment, the computer systems of client user 102 and servers 104-106 are a server system, such as IBM RS/6000 workstations and servers running the AIX operating system.

In an embodiment of the present invention, the network 108 is a circuit switched network, such as the Public Service Telephone Network (PSTN). In another embodiment, the network 108 is a packet switched network. The packet switched network is a wide area network (WAN), such as the global Internet, a private WAN, a local area network (LAN), a telecommunications network or any combination of the above-mentioned networks. In yet another embodiment, the structure of the network 108 is a wired network, a wireless network, a broadcast network or a point-to-point network.

Figure 2:
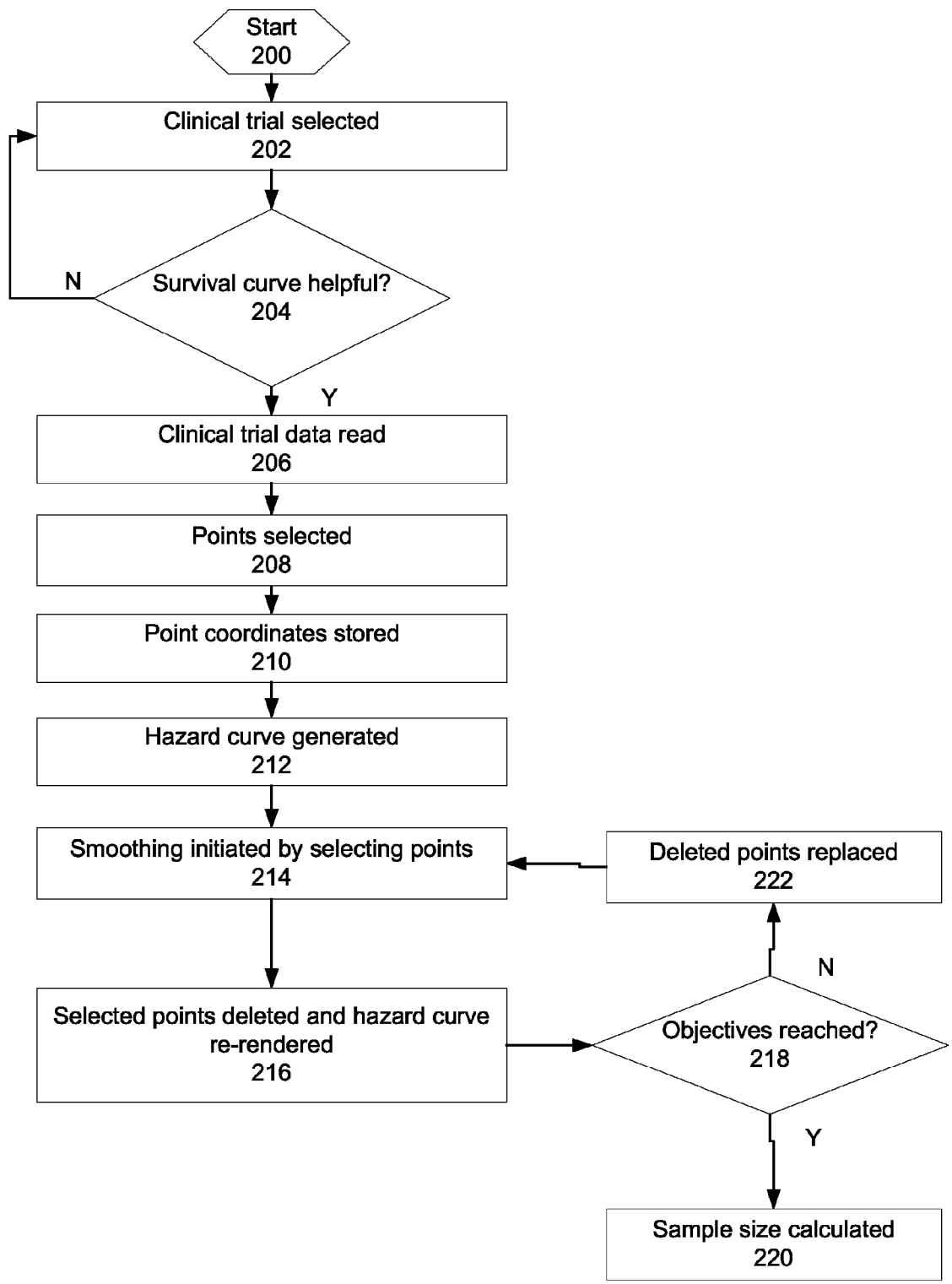
FIG. 2 is an illustration of a flowchart depicting the control flow of the automated process for calculating an appropriate sample size for a clinical trial based on already existing clinical trial data, in accordance with one embodiment of the present invention.

FIG. 2 is an illustration of a flowchart depicting the control flow of the automated process for calculating an appropriate sample size for a clinical trial based on already existing clinical trial data, in accordance with one embodiment of the present invention. The flowchart of FIG. 2 depicts the process performed by program logic 150 in calculating an appropriate sample size for a user's clinical trial (referred to as the instant clinical trial) of a treatment (referred to as the instant treatment) based on already-existing clinical trial data. The flow chart of FIG. 2 starts with step 200 and flows directly to step 202.

In step 202, a survival curve from a previous clinical trial for a treatment is selected. A survival curve is a curve that shows the cumulative probability of an event, such as death, attributable to a treatment over time. Various factors are considered when determining how to select an already-completed clinical trial from which the survival curve will be garnered, including: similarities in the population of the already-completed clinical trial and the population of the instant clinical trial, similarities in the disease of the population of the already-completed clinical trial and the disease of the population of the instant clinical trial, similarities in the demographic characteristics (age, sex and race, for example) of the already-completed clinical trial and the demographic characteristics of the instant clinical trial, similarities in the disease state (severity, and length of time since developing the medical condition) of the population of the already-completed clinical trial and the disease state of the population of the instant clinical trial, and similarities in the treatments being received by the population of the already-completed clinical trial and the treatments being received by the population of the instant clinical trial. An additional considered factor may be treatment effect data which may be similar if the instant treatment is expected to have similar characteristics to a treatment that has previously been evaluated in a trial.

Step 202 may entail a selection made by a user of client 102 interacting with a user interface. A user of client 102 may use an interface to browse through available clinical trials and associated metadata before clicking on and selecting a clinical trial and its associated survival curve. Alternatively, step 202 may be performed automatically by program logic 150. The survival curve from a previous clinical trial may be retrieved from database 110. Alternatively, the survival curve from a previous clinical trial may originate from client 102, server 104, database 110 or any combination of the three.

In step 204, it is determined whether the survival curve from the selected clinical trial will be helpful in determining the hazard curve for the instant clinical trial. A hazard curve is a curve that estimates the instantaneous probability of failing at time "t," given the set of patients still at risk just prior to time "t." It is related to the rate of change of the survival curve, and thus is similar to a derivative of the survival curve. Various factors are considered in determining whether the survival curve from the selected clinical trial(s) will be helpful in determining the hazard curve for the instant clinical trial. These factors include the factors for consideration described above for step 202. Another factor includes similarities in the control group of the selected clinical trial compared to the control group of the instant clinical trial. If the survival curve from the selected clinical trial is determined to be helpful in determining the hazard curve for the instant clinical trial, then control flows to step 206. Otherwise, control flows back to step 202 where another clinical trial is selected.

In step 206, the survival curve of the selected clinical trial(s) is read by program logic 150. The data read in step 206 may originate from client 102, server 104, database 110 or any combination of the three.

In step 208, multiple points on the survival curve of a selected clinical trial are selected. Sufficient points are selected so as to capture important or substantial variations or features in the survival curve that could reflect important deviations in the natural disease process modeled by the survival curve. The objective of step 208 is to capture different levels of the hazard function (that is derived from the survival curve), which levels reflect corresponding different levels of the risk of the underlying medical phenomenon, while eliminating variation in the hazard function due to noise. Currently, statisticians typically choose one value from the survival curve and assume the risk is constant.

In one embodiment of step 208, five or six points equally spaced on the time axis (x-axis) of the survival curve are selected. All points may be chosen at the beginning or end of a month. If there is an adjacent pair of points between which the survival curve may not appear to have constant risk, an additional point halfway between those two adjacent points may be added. If the two line segments created by the addition of a point results in two substantially different levels of the hazard curve, then the added point is retained.

Step 208 may be performed by a user interacting with a user interface. This is shown and described in greater detail in FIG. 3 below. Alternatively, step 208 may be performed automatically by program logic 150. In step 210, the x-y coordinate values of the multiple points selected in step 208 are calculated and stored.

In step 212, a hazard curve is generated based on the x-y coordinate values read in step 210. The calculated hazard curve may be in the form of a "step" or "stair" function, which is constant between any two adjacent values from the set of points selected in step 210. An x-coordinate value denotes the time from initiation of treatment, and the corresponding y-coordinate value is the probability of surviving to that time. Thus, for two adjacent time points $t1<t2$, $S(t1)$ and $S(t2)$ denotes the corresponding probabilities of survival, respectively. The hazard in the interval between t1 and t2 is approximated by the formula $\log((S(t2)-S(t1))/S(t1))/(t2-t1)$. The aforementioned formula provides the probability of failing in the interval between t1 and t2, given that the patient is still at risk at t1. An exemplary generated hazard curve is shown and described in greater detail in FIG. 4 below.

In optional step 214, smoothing of the hazard curve is initiated. This may entail selecting multiple points in the hazard curve for deletion, wherein the selected points produce perceived noise in the hazard curve. Points on the hazard curve for deletion are selected based on the objective of producing a hazard curve with the fewest number of points that summarize the curve representing the natural phenomenon underlying the curve, while eliminating jitter which appears to be noise. At least some of the variation present in the hazard curve derived in step 212 will be due to the time-varying nature of the underlying natural process described by the curve, while some of it is random noise. By analogy, a similar situation exists when a straight line is fit to a scatter plot, thereby describing a linear trend in the presence of noise. In that case, the straight line is intended to describe the underlying natural phenomenon of the linear increase (or decrease) in y as x increases. In this analogy, the scatter of points off the line is regarded as noise. Step 214 may be performed by a user interacting with a user interface, as similarly shown and described in greater detail in FIG. 3 below. Alternatively, step 214 may be performed automatically by program logic 150.

In optional step 216, selected points of the hazard curve are deleted and the hazard curve is recalculated and re-rendered, in an attempt to achieve the objectives describe in step 214. The result of step 216 is a hazard curve with constant (i.e., unchanging) segments where the selected points were deleted. See FIG. 5 below for a more detailed description of an exemplary recalculated hazard curve.

In step 218, the resultant hazard curve is visually evaluated (either by a user or the program logic 150) to determine whether the deletion produced a re-rendered hazard curve which more closely achieves the objectives described in step 214. If the resulting hazard curve reaches the stated objectives, then control flows to step 220. If the resulting hazard curve does not reach the stated objectives, then control flows to step 222 where the deleted points are replaced and then control flows back to step 214 where a different set of points can be selected.

In step 220, the appropriate sample size of the user's clinical trial is calculated using a Markov model based on the hazard curve. A Markov model is a stochastic process using a mathematical process for the random evolution of a system. A Markov model takes various factors of a clinical trial into account, such as: the amount of time it takes for a treatment to show its efficacy, the amount of time a treatment maintains its efficacy, patients taking all of their prescribed medications, patients taking all of their medications only part of the time, patients taking some of their medications all of the time, patients taking none of their medications, patients dying of an unrelated event before the target event, etc.

The Markov model provides a way of simultaneously including many real-world factors and allows a statistician to predict the appearance of the entire survival curve. This allows calculation of sample size based on a realistic projection of the entire survival curve, as opposed to simply taking a survival probability from the prior trial, and entering that probability into a formula, without consideration of how the risk changes over time and other factors.

Following is a more detailed explanation of how the Markov model can be used to calculate a sample size for a clinical trial of a treatment. A clinical survival trial can be modeled as several concurrent and interdependent stochastic processes. Each treatment group is modeled separately. The primary process is the failure process. In this process, each patient who is still at risk has a probability of failing (i.e., having the target event) as exposure to the treatment progresses. This probability can be, and often is, time-dependent. Initially, patients are assumed to comply with their assigned therapy upon entering the trial. Frequently, patients stop complying with their assigned therapy as time progresses. Each patient who is still complying with assigned therapy has a probability of failing to continue to comply as time progresses. This risk of becoming noncompliant is often time-dependent.

Competing risks refer to a situation in which other processes interfere with one's ability to evaluate the primary or target process. For example, if the trial is designed to evaluate the effects of a new treatment on heart attacks, then death from cancer or some other disease prior to observing a heart attack would interfere with observations of the time of heart attack for that patient. The risk of succumbing to a competing risk is often time-dependent. Typically, in clinical survival trials, there is a fixed calendar start and calendar conclusion of the trial, and each patient, once enrolled, is followed to the conclusion of the trial. Patients who are enrolled later will have less exposure time. Enrollment is a stochastic process, and the probability of enrollment is often time-dependent. The treatment effect of a therapy or treatment may also be time-dependent. The Markov model allows the statistician to simultaneously model all of these processes, and allows the time-dependent risks to be included in the model.

Running the Markov model on these simultaneous processes results in projected survival curves for each of the treatment groups. Each of the survival curves reflects the time-dependent nature of the contributing processes. The sample size for the trial is then calculated using the projected survival curves. The time-dependent nature of the survival curves from previous trials, as described above, is used as input for the Markov model.

As an alternative to the Markov model in step 220, simulation methods can be used. The simulation method begins with an initial guess at the sample size. The simulation method involves generating data from a hypothetical clinical trial (using a sample size of the initial guess) and analyzing the resulting data. Based on that analysis, the simulated trial is declared a success or failure. This process is repeated many (perhaps thousands of) times, and the proportion of successes provides an estimate of the appropriateness of the sample size of the initial guess. If the proportion of successes is smaller (larger) than desired, the sample size is replaced with a larger (smaller) sample size, and the process is repeated. The sample size is adjusted until a sample size is found that provides an adequate proportion of successes via the simulations. In generating data from the hypothetical clinical trial, all of the characteristics of the concurrent stochastic processes included in the Markov model must be included in the simulation model. For example, if the failure process for the Markov model was time dependent, then the simulated data must be based on a failure distribution with the same time-dependencies. This also applies to the noncompliance process, the competing risks process, etc.

Figure 3:
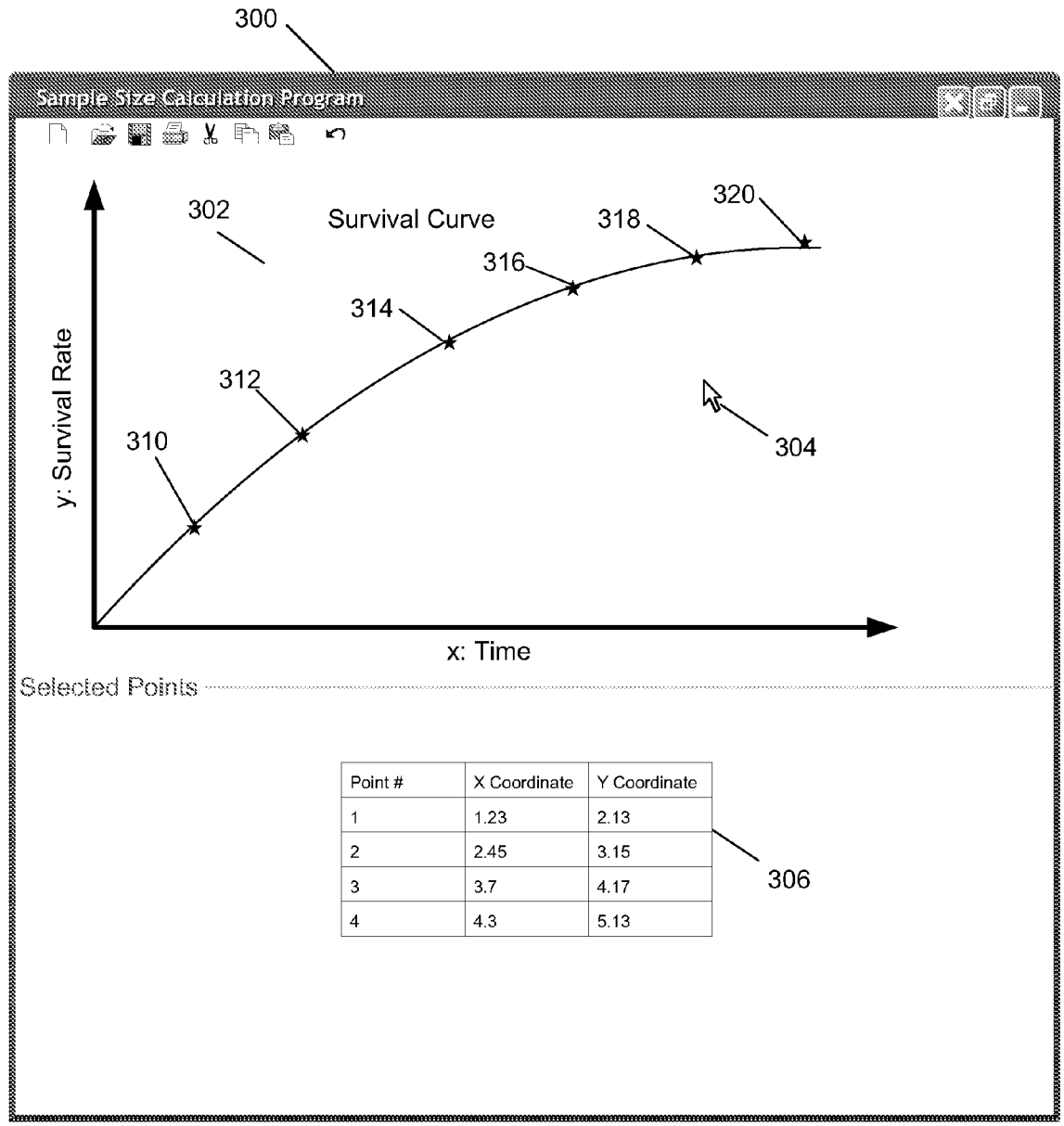
FIG. 3 is an illustration of a user interface utilized by a user to select points of a survival curve, in accordance with one embodiment of the present invention.

FIG. 3 is an illustration of a user interface 300 utilized by a user to select points of a survival curve, in accordance with one embodiment of the present invention. FIG. 3 illustrates one embodiment of the process of step 208, wherein multiple points 310-320 on the survival curve 302 of a selected clinical trial are selected by a user. The user may use a mouse pointer 304 to click on points 310-320 on the survival curve. As points are selected, the corresponding x-y coordinates are displayed below in display field 306

Figure 4:
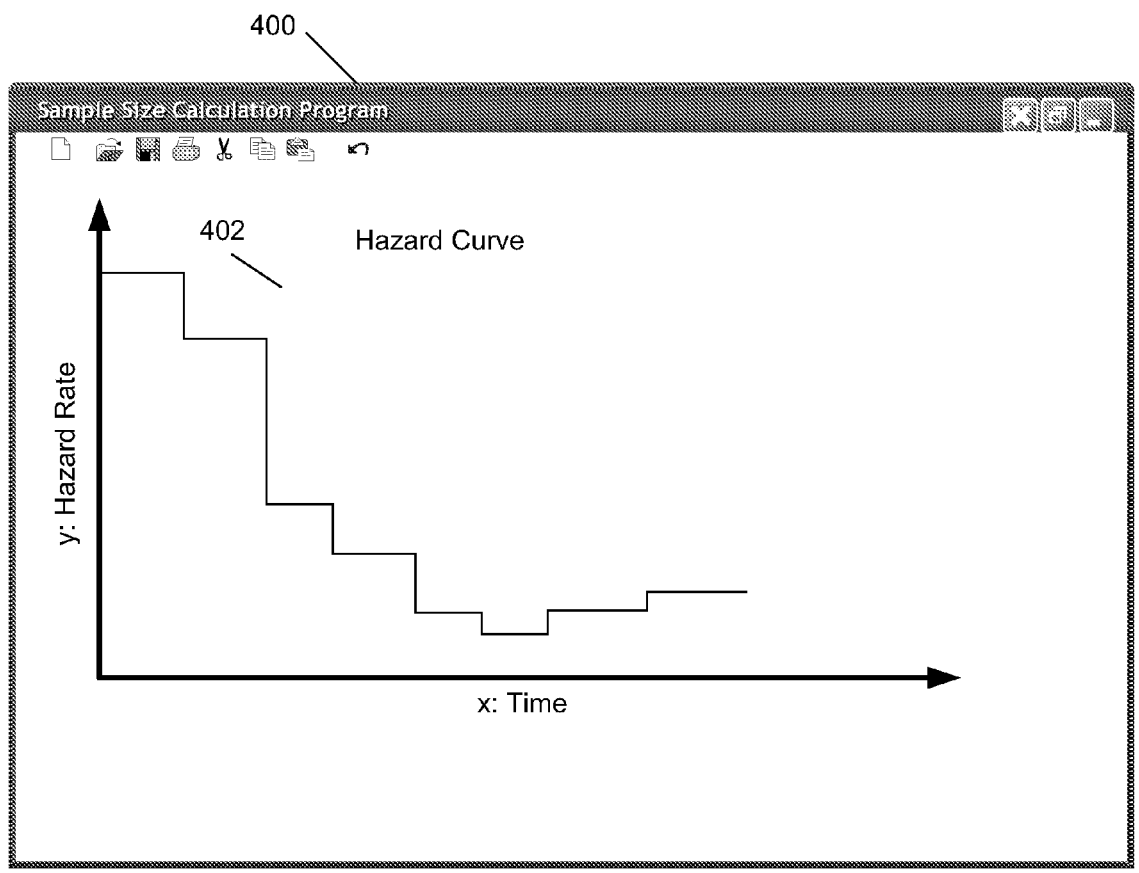
FIG. 4 is an illustration of a user interface utilized to display a hazard curve to a user, in accordance with one embodiment of the present invention.

FIG. 4 is an illustration of a user interface 400 utilized to display a hazard curve 402 to a user, in accordance with one embodiment of the present invention. FIG. 4 illustrates one embodiment of the hazard curve generated in step 212 above. The hazard curve is generated based on the x-y coordinate values read in step 210. The calculated hazard curve may be in the form of a "step" or "stair" function, which is constant between any two adjacent values from the set of points selected in step 210.

Figure 5:
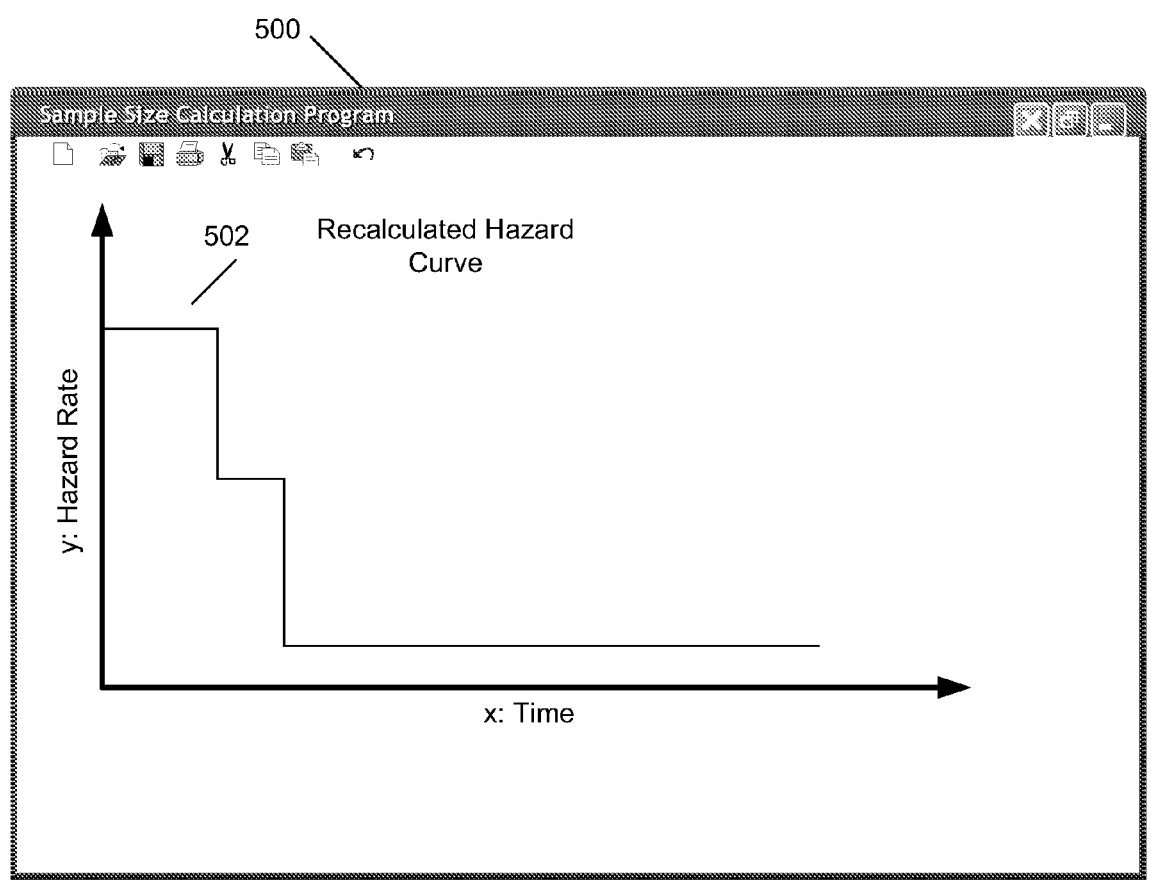
FIG. 5 is an illustration of a user interface utilized to display a recalculated hazard curve to a user, in accordance with one embodiment of the present invention.

FIG. 5 is an illustration of a user interface 500 utilized to display a recalculated hazard curve 502 to a user, in accordance with one embodiment of the present invention. FIG. 5 illustrates one embodiment of the recalculated hazard curve generated in step 216 above. The result of step 216 is a hazard curve 502 with constant (i.e., unchanging) segments where the selected points were deleted.

The present invention is advantageous because it provides a more accurate sample size estimate for a clinical trial of a treatment. Thus, the present invention increases the efficacy and efficiency of a clinical trial by providing a sample size that is not too small (thereby lowering the probability of detecting a treatment effect, assuming that such a treatment effect exists) and not too large (thereby increasing costs). Additionally, the present invention utilizes already existing clinical trial data, thereby re-using verified data, increasing precision and accuracy and lowering costs.

Embodiments of the invention can take the form of an entirely hardware embodiment, an entirely software embodiment or an embodiment containing both hardware and software elements. In a preferred embodiment, the invention is implemented in software, which includes but is not limited to firmware, resident software, microcode, and the like. Furthermore, the invention can take the form of a computer program product accessible from a computer-usable or computer-readable medium providing program code for use by or in connection with a computer or any instruction execution system.

For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

I claim:

1. A computer for calculating a sample size for a first clinical trial of a first treatment, the computer comprising:
   a memory storage;
   a network connection device communicatively coupled with the communications network; and
   a processing device coupled to the memory storage, wherein the processing device is operative for:
   reading, via the network connection device coupled with the communications network, data from a database of a first computer connected to the communications network, wherein the data comprises a plurality of survival curves from clinical trials;
   calculating a similarity between the first clinical trial and a clinical trial of each survival curve from the plurality of survival curves, wherein a similarity between clinical trials is calculated based on similarities in a disease of populations of clinical trials, similarities in treatments received by populations of the clinical trials and similarities in control groups of the clinical trials;
   selecting from the database of the first computer a second survival curve from a second clinical trial for a second treatment, wherein the second clinical trial was calculated to have a highest similarity to the first clinical trial from the set of clinical trials of the plurality of survival curves;
   reading, via the network connection device coupled with the communications network, the second survival curve that was selected from the database of the first computer;
   automatically selecting from about five points to about six points on the second survival curve, wherein all of the points that were selected correspond to a beginning of a calendar month;
   storing x-y coordinates for each of the points that were selected;

automatically generating a hazard curve based on the x-y coordinates that were stored, wherein the hazard curve is a step function and wherein a value of the step function between a first time point t1 and a second time point t2 is calculated using the formula:

$$value=\log((S(t2)-S(t1))/S(t1))/(t2-t1)$$

wherein function S(t) provides a value of the second survival curve at a given time point;
smoothing the hazard curve, wherein smoothing comprises selecting multiple points in the hazard curve that correspond to noise, deleting the multiple points in the hazard curve that were selected, and re-rendering the hazard curve to reflect the multiple points that were deleted; and
calculating a sample size for the first clinical trial using a Markov model based on the hazard curve, wherein the Markov model takes the following data into account: efficacy of the first treatment and an amount of a medication taken by patients of the first treatment.

2. The computer of claim 1, wherein the step of reading data from a database of a first computer further comprises:
reading, via the network connection device coupled with the communications network, data from the database of the first computer connected to the communications network, wherein the data comprises metadata about the plurality of survival curves from clinical trials.

3. The computer of claim 2, wherein the step of selecting a second survival curve further comprises:
receiving via a user interface a selection identifying the second survival curve from the second clinical trial for the second treatment.

4. The computer of claim 3, wherein the step of selecting points on the second survival curve further comprises:
receiving via the user interface a selection identifying all of the points that were selected from the second survival curve.

5. The computer of claim 4, wherein the step of generating a hazard curve further comprises:
generating a hazard curve based on the x-y coordinates that were stored, wherein the hazard curve is a stair function.

6. The computer of claim 5, further comprising a step after the step of reading the second survival curve, wherein the step comprises:
determining that the second survival curve that was selected from the database of the first computer meets criteria for calculating a sample size for a first clinical trial, by determining a similarity between a control group of the first clinical trial and a control group of the second clinical trial.

7. The computer of claim 3, wherein the step of selecting points on the second survival curve further comprises:
selecting from about five points to about six points on the second survival curve, wherein the five or six points are equally spaced on the second survival curve.

8. The computer of claim 7, further comprising:
identifying any line segment between the five or six points on the second survival curve that are not substantially straight; and
selecting an additional point on the second survival curve at a midpoint of any line segment that was identified as not being substantially straight.

9. A computer for calculating a sample size for a first clinical trial of a first treatment, the computer comprising:
a memory storage;
a network connection device communicatively coupled with the communications network; and
a processing device coupled to the memory storage, wherein the processing device is operative for:
reading, via the network connection device coupled with the communications network, data from a database of a first computer connected to the communications network, wherein the data comprises a plurality of survival curves from clinical trials;
calculating a similarity between the first clinical trial and a clinical trial of each survival curve from the plurality of survival curves, wherein a similarity between clinical trials is calculated based on similarities in a disease of populations of clinical trials, similarities in treatments received by populations of the clinical trials and similarities in control groups of the clinical trials;
selecting from the database of the first computer a second survival curve from a second clinical trial for a second treatment, wherein the second clinical trial was calculated to have a highest similarity to the first clinical trial from the set of clinical trials of the plurality of survival curves;
reading, via the network connection device coupled with the communications network, the second survival curve that was selected from the database of the first computer;
automatically selecting from about five points to about six points equally spaced on the second survival curve, wherein all of the points that were selected correspond to a beginning of a calendar month;
storing x-y coordinates for each of the points that were selected;
automatically generating a hazard curve, wherein the hazard curve is based on the x-y coordinates that were stored, wherein the hazard curve is a step function and wherein a value of the step function between a first time point t1 and a second time point t2 is calculated using the formula:

$$value=\log((S(t2)-S(t1))/S(t1))/(t2-t1)$$

wherein function S(t) provides a value of the second survival curve at a given time point;
smoothing the hazard curve, wherein smoothing comprises selecting multiple points in the hazard curve that correspond to noise, deleting the multiple points in the hazard curve that were selected, and re-rendering the hazard curve to reflect the multiple points that were deleted; and
calculating a sample size for the first clinical trial using a Markov model based on the hazard curve, wherein the Markov model takes the following data into account: efficacy of the first treatment and an amount of a medication taken by patients of the first treatment.

10. The computer of claim 9, wherein the step of reading data from a database of a first computer further comprises:
reading, via the network connection device coupled with the communications network, data from the database of the first computer connected to the communications network, wherein the data comprises metadata about the plurality of survival curves from clinical trials.

11. The computer of claim 10, wherein the step of selecting a second survival curve further comprises:
receiving via a user interface a selection identifying the second survival curve from the second clinical trial for the second treatment.

12. The computer of claim 11, wherein the step of selecting points on the second survival curve further comprises:

receiving via the user interface a selection identifying all of the points that were selected from the second survival curve.

13. The computer of claim 12, further comprising a step after the step of reading the second survival curve, wherein the step comprises:

determining that the second survival curve that was selected from the database of the first computer meets criteria for calculating a sample size for a first clinical trial, by determining a similarity between a control group of the first clinical trial and a control group of the second clinical trial.

14. The computer of claim 13, wherein the step of selecting points on the second survival curve further comprises:

identifying any line segment between the five or six points on the second survival curve that are not substantially straight; and selecting an additional point on the survival curve at a midpoint of any line segment that was identified as not being substantially straight.

* * * * *